(12) United States Patent
Jos et al.

(10) Patent No.: US 10,918,320 B2
(45) Date of Patent: Feb. 16, 2021

(54) METHOD OF PREDICTING BLOOD GLUCOSE LEVEL USING NEAR-INFRARED (NIR) SPECTROSCOPY DATA

(71) Applicant: SAMSUNG ELECTRONICS CO., LTD., Suwon-si (KR)

(72) Inventors: Sujit Jos, Bangalore (IN); Kiran Bynam, Bangalore (IN); So Young Lee, Daejeon (KR); Gorish Aggarwal, Bangalore (IN); Srikanth Mallavarapu Rama, Bangalore (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 386 days.

(21) Appl. No.: 15/970,461

(22) Filed: May 3, 2018

(65) Prior Publication Data
US 2018/0317817 A1 Nov. 8, 2018

(30) Foreign Application Priority Data
May 5, 2017 (IN) .............................. 201741015911

(51) Int. Cl.
| | | |
|---|---|---|
| *A61B 5/1455* | (2006.01) | |
| *G01J 3/28* | (2006.01) | |
| *A61B 5/145* | (2006.01) | |
| *A61B 5/00* | (2006.01) | |
| *G01N 21/359* | (2014.01) | |

(52) U.S. Cl.
CPC .......... *A61B 5/1455* (2013.01); *A61B 5/0075* (2013.01); *A61B 5/14532* (2013.01); *A61B 5/7267* (2013.01); *A61B 5/7275* (2013.01); *G01J 3/28* (2013.01); *G01N 21/359* (2013.01)

(58) Field of Classification Search
CPC ..... A61B 5/14532; A61B 5/1455; A61B 5/72; A61B 5/7271
See application file for complete search history.

(56) References Cited

U.S. PATENT DOCUMENTS

| | | |
|---|---|---|
| 5,957,841 A | 9/1999 | Maruo et al. |
| RE36,474 E | 12/1999 | Stark |
| 6,529,767 B1 | 3/2003 | Woo et al. |
| 6,968,221 B2 | 11/2005 | Rosenthal |
| 7,343,185 B2 | 3/2008 | Samsoondar et al. |
| 7,409,239 B2 | 8/2008 | Chung et al. |
| 8,190,551 B2 | 5/2012 | Busch et al. |
| 8,275,433 B2 | 9/2012 | Yamakoshi |
| 2006/0167350 A1* | 7/2006 | Monfre ............... A61B 5/1455 600/322 |
| 2015/0025340 A1 | 1/2015 | Kanai et al. |
| 2016/0256114 A1* | 9/2016 | Chen ................. A61B 5/14532 |

FOREIGN PATENT DOCUMENTS

| | | |
|---|---|---|
| JP | 2010-66280 A | 3/2010 |
| JP | 2012-191969 A | 10/2012 |
| KR | 10-2016-0037507 A | 4/2016 |

* cited by examiner

*Primary Examiner* — Eric F Winakur
(74) *Attorney, Agent, or Firm* — Sughrue Mion, PLLC

(57) ABSTRACT

A method for predicting a blood glucose level using a near-Infrared (NIR) spectrometer is provided. The method may include obtaining a feature set from an NIR glucose spectra; and predicting glucose values from the feature set based on a binary classification of the NIR glucose spectra and an in-class prediction of glucose using Machine Learning Regression.

7 Claims, 8 Drawing Sheets

METHOD OF PREDICTING BLOOD GLUCOSE LEVEL USING NEAR-INFRARED (NIR) SPECTROSCOPY DATA

CROSS-REFERENCE TO RELATED APPLICATION

This application claims priority from Indian Patent Application No. 201741015911, filed on May 5, 2017 in the Indian Patent Office, the disclosure of which is incorporated herein by reference in its entirety.

BACKGROUND

1. Field

Apparatuses and methods consistent with exemplary embodiments relate to glucose monitoring, and more particularly relate to predicting a blood glucose level using Near-Infrared (NIR) Spectroscopy data.

2. Description of the Related Art

Glucose monitoring may be used to measure the level of glucose in a blood sample. The glucose monitoring may be performed either invasively or non-invasively. In the invasive method, the skin of a person is pierced to obtain the blood sample. In the non-invasive method, collection of the blood sample may not be required to measure the glucose level, and instead Mid-Infrared (Mid-IR) spectroscopy, Near-Infrared (NIR) spectroscopy, or Raman spectroscopy may be used. The NIR spectroscopy has been used for continuous glucose monitoring, in which NIR waves are generated to pass through the skin and a spectrum indicating absorption of the NIR waves by the blood underneath the skin is used in determining the glucose level. The absorption of the NIR waves is defined by BEER-Lambert law:

$$A = \log\left(\frac{I}{I_0}\right) = \epsilon C d$$

Where $\epsilon$ is an absorption co-efficient,
C is a concentration of a component in sample, and
d is a penetration depth.

If the sample includes different constituents, then the overall absorption is obtained based on the following equation:

$$A = \epsilon\_1 C\_1 d + \epsilon\_2 C\_2 d + \ldots + \epsilon\_n C\_n d$$

The NIR absorption spectrum indicates absorption of several components such as water, fat, protein (Collagen and Keratin), Amino acids, elastin and Glucose. Therefore, $$A\_NIR = A\_Water + A\_Cholesterol + A\_Collagen + A\_Keratin + A\_elastin + A\_acid + A\_Glucose$$

Further, the concentration of glucose in an interstitial liquid is given by $$C\_Glucose = A\_Glucose / A\_Water$$

Thus, glucose monitoring is very challenging as the values of glucose absorption is of several orders lesser than other constituents and many times, the glucose information is distorted due to the noise components of the NIR data. The order of concentration of different constituents are shown in the below table.

| Constituent | Water | Fat | Protein | Elastin/Acid | Glucose |
|---|---|---|---|---|---|
| Order of concentration (~) | $10^0$ | $10^{-1}$ | $10^{-3}$ | $10^{-3}$ | $10^{-4}$ |

Therefore, there is a need for a method of predicting blood glucose values with a high accuracy using NIR spectroscopy data.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide a method of predicting blood glucose level using Near-Infrared (NIR) spectroscopy data.

According to an aspect of an exemplary embodiment, there is provided a method of predicting a blood glucose level using near-infrared (NIR) spectroscopy data. The method may include: obtaining a feature set from an NIR glucose spectra; and predicting glucose values from the feature set based on a binary classification of the NIR glucose spectra and an in-class prediction of glucose using Machine Learning Regression.

The obtaining the feature set may include: obtaining a raw feature set from NIR glucose spectra samples associated with different blood glucose levels; identifying one or more glucose dependent features present in the NIR glucose spectra samples; and removing collinearity from the identified one or more glucose dependent features to obtain the feature set.

The identifying one or more glucose dependent features present in the NIR glucose spectra samples may include: obtaining a low variance set of features that exhibits a low variance for a same glucose value in the NIR glucose spectra; obtaining a high variance set of features that varies in accordance with a change in glucose levels; and obtaining the one or more glucose dependent features as features which are common to both of the low variance set and the high variance set.

The predicting the glucose values may include: obtaining a glucose plot representing a plurality of glucose values at different time instances; and classifying the plurality of glucose values based on the time instances into a first bin and a second bin, wherein the first bin may correspond to glucose values with a rise time period and the second bin may correspond to glucose values with a decay time period.

The method may further include: generating an artificial neural network (ANN) framework based a classification model that classifies the NIR glucose spectra into a first bin and a second bin using a backpropagation method; and classifying the NIR glucose spectra based on the generated classification model.

The predicting the glucose values may include: segregating the NIR spectroscopy data into one or more binary classes; generating a regression model for each of the one or more binary classes; and predicting the glucose values based on the generated regression model for each class.

According to an aspect of another exemplary embodiment, there is provided a glucose prediction device including at least one or more processors. The at least one or more processors may include: a feature set extraction unit configured to obtain a feature set from an NIR glucose spectra;

and a prediction unit configured to predict glucose values from the feature set based on a binary classification of the NIR glucose spectra and an in-class prediction of glucose using Machine Learning Regression.

The feature set extraction unit may include: a raw feature extraction unit configured to extract a raw feature set from NIR glucose spectra samples associated with different blood glucose levels; a glucose dependent features isolation unit configured to identify one or more glucose dependent features present in the NIR glucose spectra samples; and a collinearity removal unit configured to remove collinearity from the identified one or more glucose dependent features to obtain the feature set.

The glucose dependent features isolation unit may be further configured to obtain a low variance set of features that represents a low variance for a same glucose value in the NIR glucose spectra, obtain a high variance set of features that varies in accordance with a change in glucose levels, and obtain the one or more glucose dependent features as features which are common to both of the low variance set and the high variance set.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
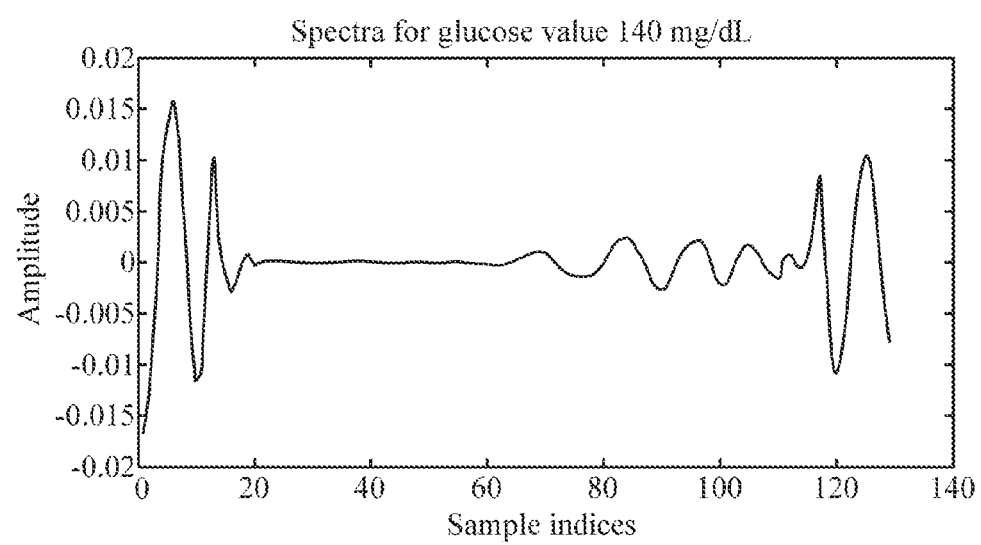
FIG. 1 illustrates a preprocessed glucose spectrum for a glucose value of 140 mg/dL, according to a comparative example.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

The specification may refer to "an", "one" or "some" embodiment(s) in several locations. This does not necessarily imply that each such reference is to the same embodiment(s), or that the feature only applies to a single embodiment. Single features of different embodiments may also be combined to provide other embodiments.

As used herein, the singular forms "a", "an" and "the" are intended to include the plural forms as well, unless expressly stated otherwise. It will be further understood that the terms "includes", "comprises", "including" and/or "comprising" when used in this specification, specify the presence of stated features, integers, steps, operations, elements and/or components, but do not preclude the presence or addition of one or more other features, integers, steps, operations, elements, components, and/or groups thereof. As used herein, the term "and/or" includes any and all combinations and arrangements of one or more of the associated listed items.

Expressions such as "at least one of," when preceding a list of elements, modify the entire list of elements and do not modify the individual elements of the list.

Unless otherwise defined, all terms (including technical and scientific terms) used herein have the same meaning as commonly understood by one of ordinary skill in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Throughout the specification, the terms "bins" and "classes" are interchangeably used.

One or more exemplary embodiments provide a method for predicting blood glucose level using Near-Infrared (NIR) spectroscopy data. The method includes calculating a blood-glucose level non-invasively based on the NIR spectroscopy data. A prediction method may be used to measure the blood glucose level. The prediction method may include a two-stage algorithm for predicting the blood glucose level.

The prediction method is explained herein in detail. Firstly, the blood glucose level is obtained using a standard invasive procedure. Then, a non-invasive spectral scan is performed on a person using near-Infrared spectrometer to obtain raw NIR spectra. The raw NIR spectra is labelled by the glucose level which is obtained from the invasive procedure. The obtained raw NIR spectra is preprocessed further to obtain glucose spectra. An exemplary preprocessed glucose spectra for a glucose value of 140 mg/dL is shown in FIG. 1. The obtained glucose spectra may contain 129 samples which are referred to as features. The glucose spectra and the associated glucose values may be arranged into the form of the following matrix X, which is referred as data matrix.

$$X = \begin{bmatrix} g^1 & x_0^1 & x_1^1 & \ldots & x_{129}^1 \\ g^2 & x_0^2 & x_1^2 & \ldots & x_{129}^2 \\ & & \ldots & & \\ g^N & x_0^N & x_1^N & \ldots & x_{129}^N \end{bmatrix}$$

Here, element $g^k$ is a glucose value associated with $k^{th}$ spectrum and includes 129 samples $x_0^k \, x_1^k \ldots x_{128}^k$. $N \approx 200$ is the total number of samples obtained per day, the samples being obtained consecutively every minute till N samples are accumulated.

Figure 2:
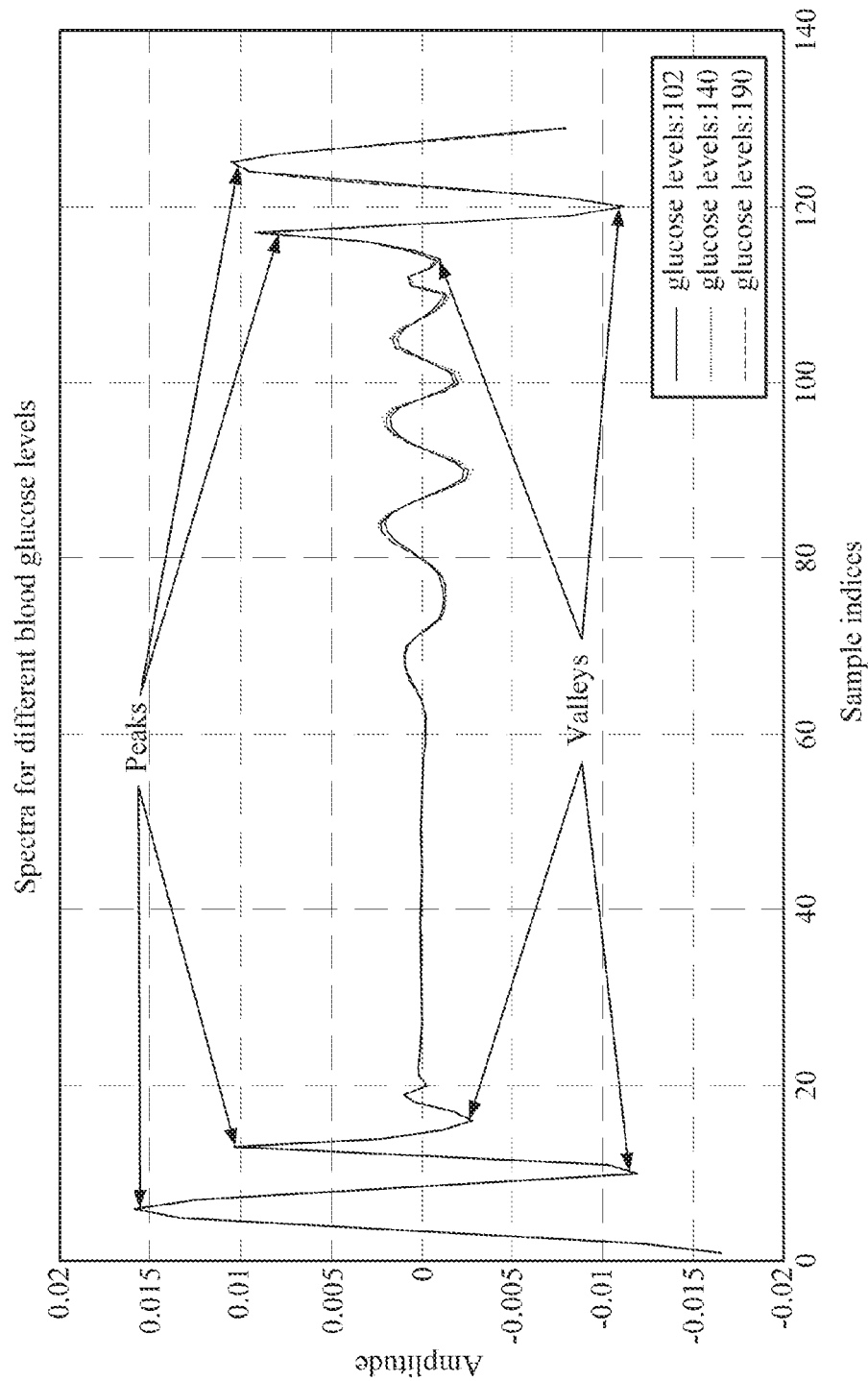
FIG. 2 illustrates different glucose spectra obtained for different levels of glucose values, according to an exemplary embodiment.

Further, glucose spectra for different levels of glucose values such as for 102 mg/dL, 140 mg/dL, 190 mg/dL are obtained and shown in FIG. 2. As shown in FIG. 2, variations in the spectra from one glucose value to another occurs primarily around edges of the spectra. The following features are arrived at to capture the information at the edges.

Peak to valley ratio: The peak to valley ratio R_pv is defined as the ratio of the mean of values at the peaks to the mean of the values at the valleys.

Peak to peak ratio: The peak to peak ratio $R_{pp}$) is defined as the ratio of values at different peaks in the spectrum waveform.

Mean peak value: The mean peak value $\mu_p$ is obtained as the mean of values occurring at a subset of all peaks.

Spectra energy ($E_s$): The spectra energy $E_s$ represents the energy of a signal and it is defined as $E_s=\Sigma_n s_n^2$. The first two features Peak to valley ratio and to peak to peak ratio features capture relative information in the peaks/valleys which is expected to provide a desired output at different signal-to-noise ratios (SNRs) while the latter features correspond to an absolute span of a given spectra.

Spectra samples: Apart from the above four features, the 129 sample of glucose spectra are called as spectra samples. Therefore, the total of 133 features including 129 features of NIR spectra and four features described above constitutes the raw feature set for model training.

After obtaining the raw feature set, glucose dependent features may be obtained from the set of 133 features. Among the 133 features, a few features exhibit low variance for the same glucose value in the spectral data set and a few features vary highly with the change in glucose values. These features are referred to as low variance features and high variance features, respectively. Now, from both of the low variance and high variance features, a set of glucose dependent features which are common to both of the low variance set and high variance set are selected as the glucose dependent features. The corresponding method steps are illustrated in FIG. 3.

Figure 3:
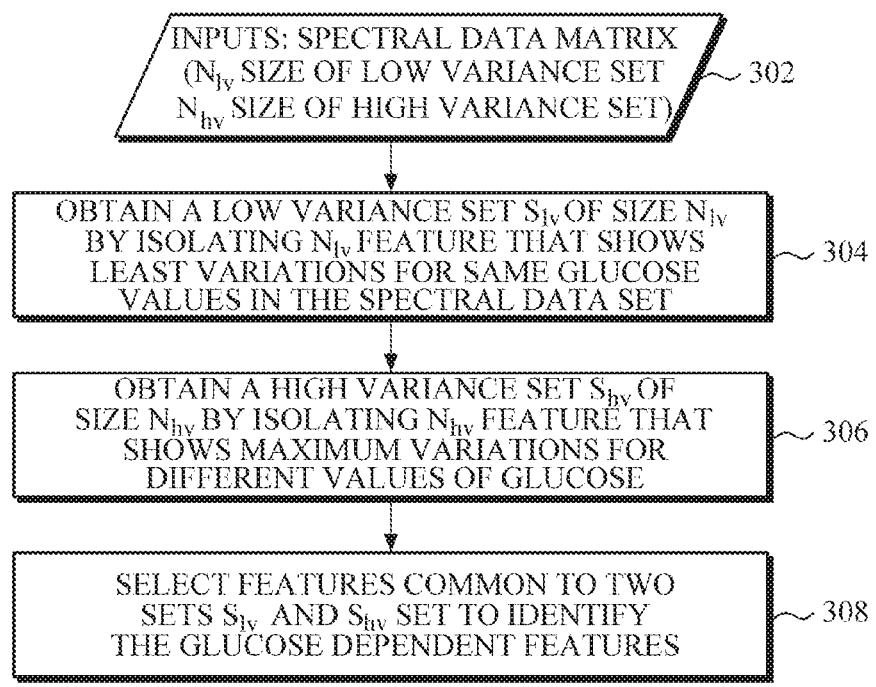
FIG. 3 is a flow chart illustrating a method of isolating glucose dependent features from a raw feature set, according to an exemplary embodiment.

FIG. 3 is a flow chart illustrating a method of isolating glucose dependent features from a raw feature set, according to an exemplary embodiment. Firstly, the raw feature set of 133 features are classified into a high variance set $S_{hv}$ and a low variance set $S_{lv}$. In operation 302, spectral data matrix X is inputted, which includes a size $N_{lv}$ of the low variance set $S_{lv}$ and a size $N_{hv}$ of the high variance set $S_{hv}$. In operation 304, the low variance set $S_{lv}$ of the size $N_{lv}$ is obtained by isolating $N_{lv}$ features that show least variations for the same glucose value in the spectral data set. In operation 306, the high variance set $S_{hv}$ of the size $N_{hv}$ is obtained by isolating $N_{hv}$ features show maximum variations for different values of glucose. In operation 308, features that are common to both variance sets $S_{lv}$ and $S_{hv}$ are selected to identify glucose dependent features.

Figure 4:
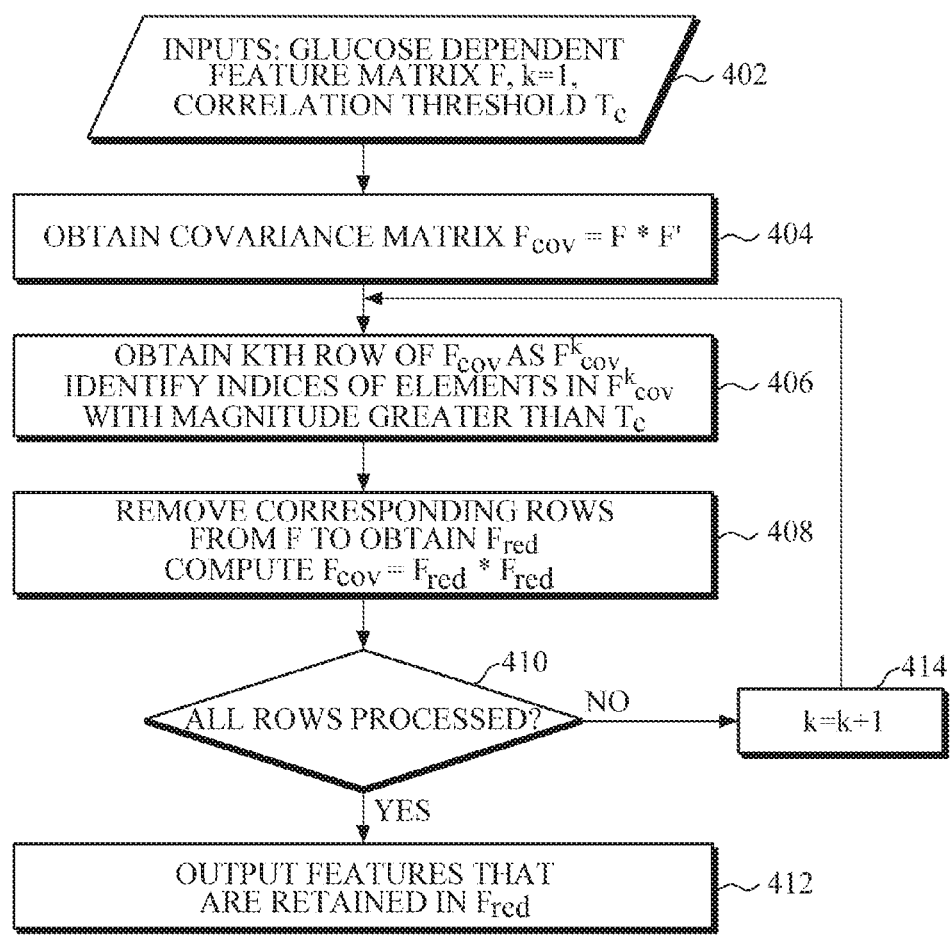
FIG. 4 is a flowchart illustrating a method of removing collinearity from extracted glucose dependent features, according to an exemplary embodiment.

FIG. 4 is a flowchart illustrating a method of removing collinearity from the glucose dependent features, according to an exemplary embodiment. The step by step procedure of removing the collinearity is explained in detail herein. In an exemplary embodiment, the glucose dependent features may have highly correlated or collinear features which tend to affect the accuracy of the glucose prediction algorithm. Thus, it may be necessary to remove collinear features from the glucose dependent features.

In operation 402, a matrix F is formed based on glucose dependent features with k=1 and $T_c$, where variable 'k' is used to index the kth row of F and $T_c$ refers to correlation threshold. In operation 404, a covariance matrix for the glucose dependent features $F_{cov}$ is obtained. In an exemplary embodiment, the $F_{cov}$ is calculated based on the following formula $$F_{cov}=F*F'$$

In operation 406, a covariance matrix for a 'k' th row $F_{cov}^k$ is obtained, and the indices of elements in the covariance matrix $F^k_{cov}$ with magnitude greater than $T_c$ are identified. Then, in operation 408, the corresponding rows whose magnitude greater than $T_c$ are removed to obtain $F_{red}$. $F_{red}$ is the matrix obtained from matrix F by removing the features with a high correlation at each step. Further, in operation 408, the covariance matrix $F_{cov}$ for $F_{red}$ is also computed. In operation 410, it is determined whether all the rows in the matrix are processed. If all the rows are not processed, the value of k is increased by 1 until processing of all the rows gets completed in operation 414. If all the rows are processed, in operation 412, final output features that are retained in $F_{red}$ are obtained.

These final output features that remain after the collinearity removal from the glucose dependent features are referred to as the feature set. Using the obtained feature set, the NIR glucose spectra is first classified using binary classification method. In this binary classification method, glucose plots for different glucose values at different time instances are considered.

Figure 5:
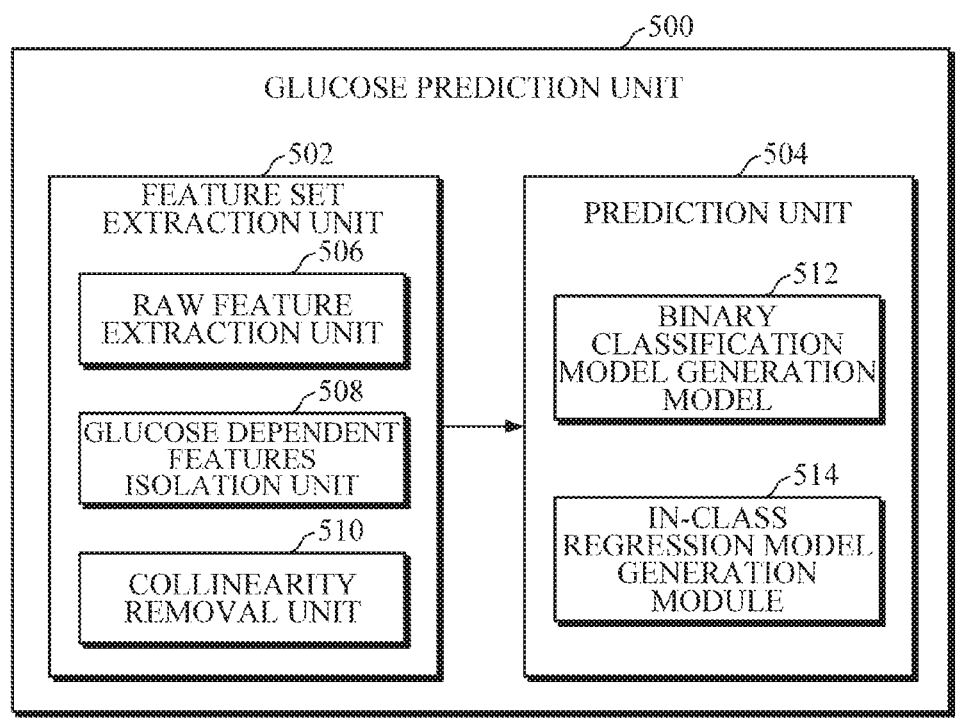
FIG. 5 is a block diagram illustrating various components of a glucose prediction unit, according to an exemplary embodiment.

FIG. 5 is a block diagram illustrating one or more components of a glucose prediction unit, according to an exemplary embodiment. As shown in FIG. 5, the glucose prediction unit 500 includes a feature set extraction unit 502, and a prediction unit 504 that predicts a blood glucose level. The feature set extraction unit 502 may include a raw feature extraction unit 506, a glucose dependent features isolation unit 508, and a collinearity removal unit 510. The prediction unit 504 may include a binary classification model generation module 512 and an in-class regression model generation module 514. The raw feature extraction unit 506, the glucose dependent features isolation unit 508, the collinearity removal unit 510, the binary classification model generation module 512, and the in-class regression model generation module 514 may be implemented with one or more processors.

The feature set extraction unit 502 may obtain a final set of glucose features for predicting blood glucose values. The feature set is obtained with the use of modules including the raw feature extraction unit 506, the glucose dependent features isolation unit 508 and the collinearity removal unit 510. The raw feature extraction unit 506 may obtain NIR spectra of a person through NIR spectrometer. The NIR spectra are then processed by the raw feature extraction unit 506 to obtain glucose spectra. The raw feature extraction unit 506 extracts 129 features from the obtained glucose spectra. The obtained glucose spectra for different glucose values are then processed by the raw feature extraction unit to obtain four more features, amounting to a total of 133 features. These 133 features are further analyzed by the glucose dependent features isolation unit 508 to extract only glucose dependent features.

The glucose dependent features isolation unit 508 first segregates the whole 133 features into a high variance set and a low variance set. The features which exhibit a low variance for the same glucose value in the spectral data set are segregated as a low variance set. The features which vary highly with the change in the glucose values are segregated as a high variance set. The glucose dependent features isolation unit 508 further identifies common features present in both the high variance and low variance data set. The identified common features are considered as glucose dependent features.

The collinearity removal unit 510 may remove collinearity from the glucose dependent features. As shown in FIG. 4, the collinearity removal unit 510 forms a matrix using glucose dependent features. Then, covariance matrix for the 'k' th row is also obtained. In that 'k'th row, indices of elements whose magnitude greater than threshold are identified and then removed to obtain the final output features that are retained in the $F_{red}$. The final output features are referred as 'feature set'. This 'feature set' is then transferred to a prediction unit for further processing.

In an exemplary embodiment, the prediction unit 504 uses the 'feature set' obtained from the feature set extraction unit 502 to generate a model to predict glucose values. The prediction unit 504 deploys a two-stage algorithm to predict a blood glucose value corresponding to a given glucose spectra. The two-stage algorithm includes a binary classification model generation module 512 and an in-class regression model generation module 514. The binary classification model generation module 512 performs training of an artificial neural network in order to obtain the binary classification model. The in-class regression model generation module 514 performs a regression training of a machine learning regression tool to obtain the in-class regression model. The regression model generated based on the two algorithms are explained herein in detail in FIG. 7.

Figure 6A:
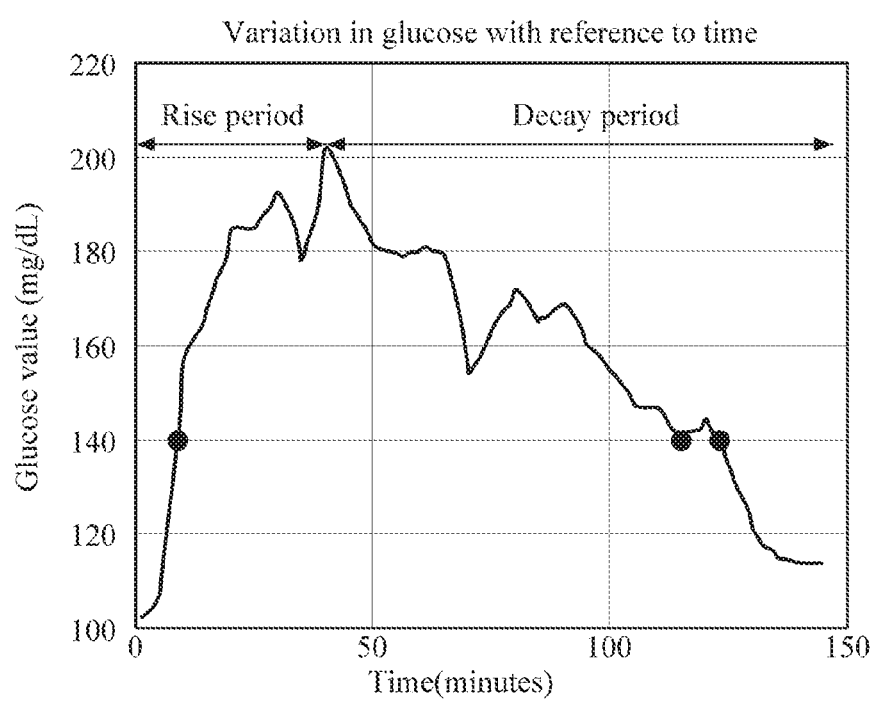
FIG. 6A illustrate variations in glucose values with respect to time of a test subject, according to an exemplary embodiment.
Figure 6B:
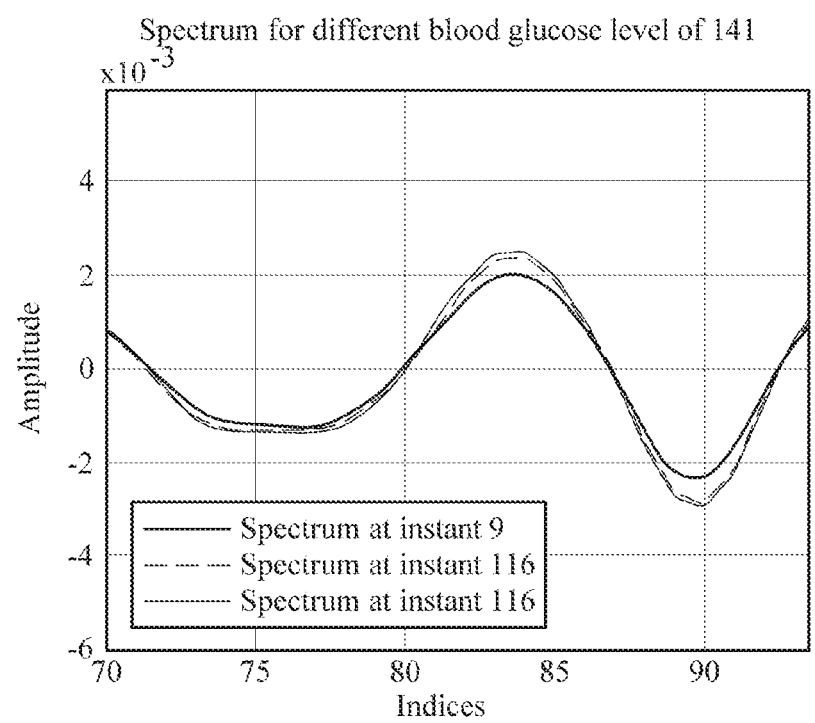
FIG. 6B shows spectra associated with a glucose value of 141 mg/dL at different instances in a glucose plot, according to an exemplary embodiment.

FIG. 6A illustrates a glucose plot obtained for glucose values at different time instances for generating a binary classification model, according to an exemplary embodiment. FIG. 6A also illustrates the instances at which a glucose value of 141 mg/dL is measured, namely at times instances 9, 116 and 122. The variation in the glucose value with respect to time including food intake is considered. Though, the spectra corresponding to the glucose value 141 looks very similar at different times, there can be small variations also. As can be seen in FIG. 6B, the spectra obtained for the same glucose value of 141 mg/dL at instant 116 and 122 are highly correlated and look dissimilar to the glucose spectrum at instant 9. The difference in the nature of spectra of the same glucose value at different instances is attributed to the nature of the transition of the glucose values. These transitions form the basis of multi-class classification of the spectra. Therefore, the entire range of glucose values is classified into two bins, namely bin 1 and bin 2. Bin 1 corresponds to glucose values with a rise period and bin 2 corresponds to glucose values with a decay period. The spectra belonging to the same bin are highly correlated. Based on this, a classification model for the binary classification is generated. An artificial neural network (ANN) based learning is deployed for binary classification of NIR spectra.

Now, using the two bins, two classes are defined namely, class-R and class-D. Class-R corresponds to a raising period and class-D corresponds to a decay period. The two classes are used in creating a classification model based on the ANN framework. The model training is performed using a backpropagation algorithm implemented in MATLAB. At first, data obtained from a test subject on the first day of an experiment, henceforth referred to as day-1 data is used for the model training. The model training for the ANN is performed using the backpropagation algorithm.

In an exemplary embodiment, the trained classification model is tested using the data obtained from the same test subject on the second day of the experiment, henceforth referred to as day-2 data. The features used for training the classification model is extracted for each of the individual spectra in the test data-set. The extracted features are provided as inputs to the model which makes prediction of the glucose values associated with individual spectra in the test data. Then, the classification accuracy for each of the class is obtained as shown in the below table for four different test subjects labelled as S1, S2, S3 and S4. For generating these results, a three layer ANN with a hidden layer of 20 nodes is considered to build the classification model.

| Test Person | Recall (True positive rate) | True negative rate | Precision | % Accuracy | F1 score |
|---|---|---|---|---|---|
| S1 | 0.9924 | 1 | 1 | 99.4 | 0.9961 |
| S2 | 1 | 0.37 | 0.86 | 87.2 | 0.9254 |
| S3 | 1 | 0.83 | 0.97 | 97.2 | 0.9832 |
| S4 | 1 | 0.87 | 0.97 | 97.7 | 0.9865 |

Once the binary classification is performed, a machine learning (ML) regression model is employed for the In-class prediction. The generation of regression model is explained in FIG. 7.

Figure 7:
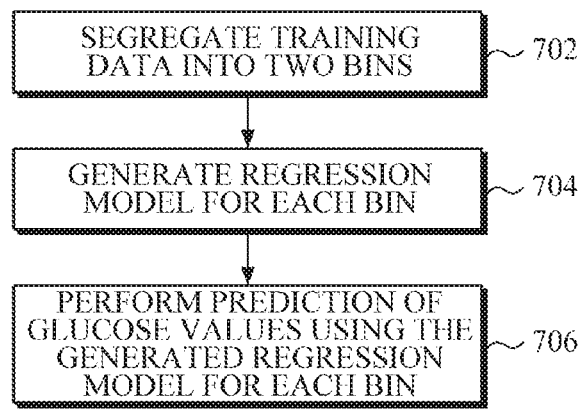
FIG. 7 is a flowchart illustrating an exemplary generation of regression model for predicting glucose values, according to an exemplary embodiment.

FIG. 7 is a flowchart illustrating a generation of regression model, according to an exemplary embodiment. In operation 702, training data is segregated into two bins corresponding to class-R and class-D, respectively. Then regression model training is performed in each individual bin to predict glucose values. The regression is carried over a given feature vector that is classified into either belonging to Bin-R or Bin-D to obtain the corresponding glucose value associated with the feature vector. The set of features used for the in-class regression remains the same as was used for training the classification model. In operation 704, the regression model is generated for each bin and in operation 706, prediction of the glucose values is performed using the generated regression model for each bin. The same is illustrated in FIG. 7. The accuracy results for the in-class regression are given in the table below. A Gaussian process regression is used for the purpose of demonstration. The day-1 data is used for training and day-2 data is used for testing, for the respective test subjects.

| Test Subject | Gaussian Process Regression | | | | | | | | |
|---|---|---|---|---|---|---|---|---|---|
| | R | | | SEP | | | MARD | | |
| | Bin | | | Bin | | | Bin | | |
| | Bin 1 | Bin 2 | $R_{Exp}$ | Bin 1 | Bin 2 | $SEP_{Exp}$ | Bin 1 | Bin 2 | $MARD_{Exp}$ |
| S1 | 0.89 | 0.92 | 0.92 | 18.86 | 19.78 | 19.61 | 0.74 | 11.04 | 10.98 |
| S2 | 0.86 | 0.81 | 0.82 | 39.84 | 31.88 | 33.50 | 37.27 | 19.19 | 22.24 |
| S6 | 0.91 | 0.89 | 0.90 | 8.10 | 8.33 | 8.29 | 4.81 | 5.17 | 5.11 |
| S7 | 0.87 | 0.88 | 0.89 | 18.31 | 13.98 | 13.02 | 5.69 | 8.14 | 7.23 |

In the table, an expected correlation coefficient $R_{Exp}$ is a weighted summation of R values of individual bins and is defined as $$R_{Exp} = \frac{n_1 R_1 + n_2 R_2}{n_1 + n_2}$$

Similarly, $SEP_{Exp} = \dfrac{n_1 SEP_1 + n_2 SEP_2}{n_1 + n_2}$, $$MARD_{Exp} = \frac{n_1 MARD_1 + n_2 MARD_2}{n_1 + n_2}$$

Here, $n_1$ and $n_2$ denote the number of samples belonging to Bin-R and Bin-D, respectively While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of predicting a blood glucose level using near-infrared (NIR) spectroscopy data, the method comprising:
   obtaining a feature set from an NIR glucose spectra; and
   predicting glucose values from the feature set based on a binary classification of the NIR glucose spectra and an in-class prediction of glucose using Machine Learning Regression,
   wherein the obtaining the feature set comprises:
      obtaining a raw feature set from NIR glucose spectra samples associated with different blood glucose levels;
      identifying one or more glucose dependent features present in the NIR glucose spectra samples; and
      removing collinearity from the identified one or more glucose dependent features to obtain the feature set.

2. The method as claimed in claim 1, wherein the identifying one or more glucose dependent features present in the NIR glucose spectra samples comprises:
   obtaining a low variance set of features that exhibits a low variance for a same glucose value in the NIR glucose spectra;
   obtaining a high variance set of features that varies in accordance with a change in glucose levels; and
   obtaining the one or more glucose dependent features as features which are common to both of the low variance set and the high variance set.

3. The method as claimed in claim 1, wherein the predicting the glucose values comprises:
   obtaining a glucose plot representing a plurality of glucose values at different time instances; and
   classifying the plurality of glucose values based on the time instances into a first bin and a second bin, wherein the first bin corresponds to glucose values with a rise time period and the second bin corresponds to glucose values with a decay time period.

4. The method as claimed in claim 3, further comprising:
   generating an artificial neural network (ANN) framework based a classification model that classifies the NIR glucose spectra into the first bin and the second bin using a backpropagation method; and
   classifying the NIR glucose spectra based on the generated classification model.

5. The method as claimed in claim 1, wherein the predicting the glucose values comprises:
   segregating the NIR spectroscopy data into one or more binary classes;
   generating a regression model for each of the one or more binary classes; and
   predicting the glucose values based on the generated regression model for each class.

6. A glucose prediction device comprising at least one or more processors, the at least one or more processors comprising:
   a feature set extraction unit configured to obtain a feature set from an NIR glucose spectra; and
   a prediction unit configured to predict glucose values from the feature set based on a binary classification of the NIR glucose spectra and an in-class prediction of glucose using Machine Learning Regression,
   wherein the feature set extraction unit comprises:
      a raw feature extraction unit configured to extract a raw feature set from NIR glucose spectra samples associated with different blood glucose levels;
      a glucose dependent features isolation unit configured to identify one or more glucose dependent features present in the NIR glucose spectra samples; and
      a collinearity removal unit configured to remove collinearity from the identified one or more glucose dependent features to obtain the feature set.

7. The glucose prediction device of claim 6, wherein the glucose dependent features isolation unit is further configured to obtain a low variance set of features that represents a low variance for a same glucose value in the NIR glucose spectra, obtain a high variance set of features that varies in accordance with a change in glucose levels, and obtain the one or more glucose dependent features as features which are common to both of the low variance set and the high variance set.

* * * * *